United States Patent [19]
Fischer et al.

[11] Patent Number: 5,445,523
[45] Date of Patent: Aug. 29, 1995

[54] SYRINGE APPARATUS AND METHODS FOR DISPENSING VISCOUS MATERIALS

[75] Inventors: Dan E. Fischer; David V. Fischer, both of Sandy, Utah

[73] Assignee: Ultradent Products, Inc., South Jordan, Utah

[21] Appl. No.: 117,398

[22] Filed: Sep. 3, 1993

[51] Int. Cl.⁶ .............................................. A61C 5/04
[52] U.S. Cl. ...................................................... 433/90
[58] Field of Search .................... 433/89, 90; 604/218, 604/232, 234, 240, 241; 222/386, 387

[56] References Cited

U.S. PATENT DOCUMENTS

| | | | |
|---|---|---|---|
| 2,515,956 | 7/1950 | Greenberg | 128/218 |
| 2,537,550 | 1/1951 | Roos | 128/218 |
| 2,754,590 | 7/1956 | Cohen | 433/90 |
| 2,778,359 | 1/1957 | Friedman | 604/232 |
| 3,462,840 | 8/1969 | Ellman | 433/90 |
| 3,811,441 | 5/1974 | Sarnoff | 604/232 X |
| 3,854,209 | 12/1974 | Franklin et al. | 433/90 |
| 3,974,831 | 8/1976 | Malmin | 433/90 X |
| 4,540,405 | 9/1985 | Miller et al. | 604/232 |
| 4,643,724 | 2/1987 | Jobe | 604/232 |
| 4,784,607 | 11/1988 | Francois | 433/90 |
| 4,801,263 | 1/1989 | Clark | 433/90 |
| 5,067,948 | 11/1991 | Haber et al. | 604/232 X |
| 5,232,459 | 8/1993 | Hjertman | 604/232 X |

OTHER PUBLICATIONS

Actual Product Sample of DMG Superlux ® Molar syringe.
Product Brochure–DMG Superlux ® Universal Bond 2, Ionisit ® Base Liner, Superlux ® Mold and Superlux ® Solar–published before Applicants' filing date.
Product Brochure–DMG Alpha ®–Fil, Alpha ®–Base and Alpha ®–Silver–published before Applicants' filing date.
Product Brochure–DMG Luxatemp, temporary crown and bridge material–published before Applicants' filing date.

Primary Examiner—Nicholas D. Lucchesi
Attorney, Agent, or Firm—Workman Nydegger Seeley

[57] ABSTRACT

Syringe assembly apparatus and associated methods are provided for use in dispensing viscous materials, such as dental compositions, in a controlled fashion. The preferred embodiment of the syringe assembly of the present invention includes a syringe body of conventional fashion, having a passageway therethrough and a discharge port communicating with the passageway. An adapter member is provided which nests within the syringe body passageway, the adapter member having a bore passing through the length thereof for receiving a viscous material to be dispensed. When the adapter is nested within the passageway of the syringe body, the bore communicates with the discharge port of the syringe body. An important feature of the invention is that the bore has a diameter substantially the same as the diameter of the discharge port at the location where the discharge port communicates with the bore. The assembly of the present invention also includes a plunger member for ejecting viscous material contained within the bore through the discharge port of the syringe body. The present invention is also directed to adapter members for use with conventional syringes.

16 Claims, 3 Drawing Sheets

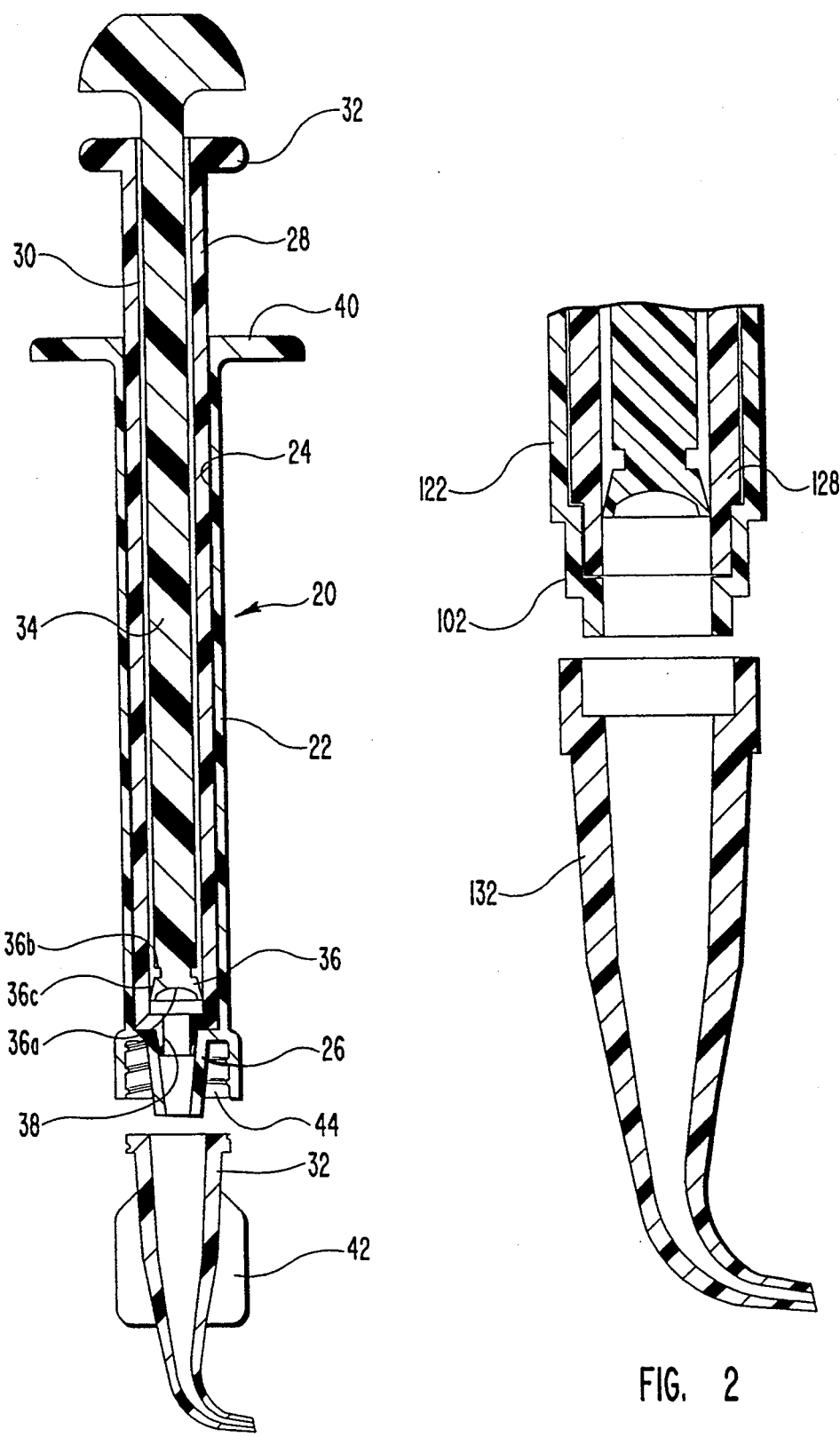

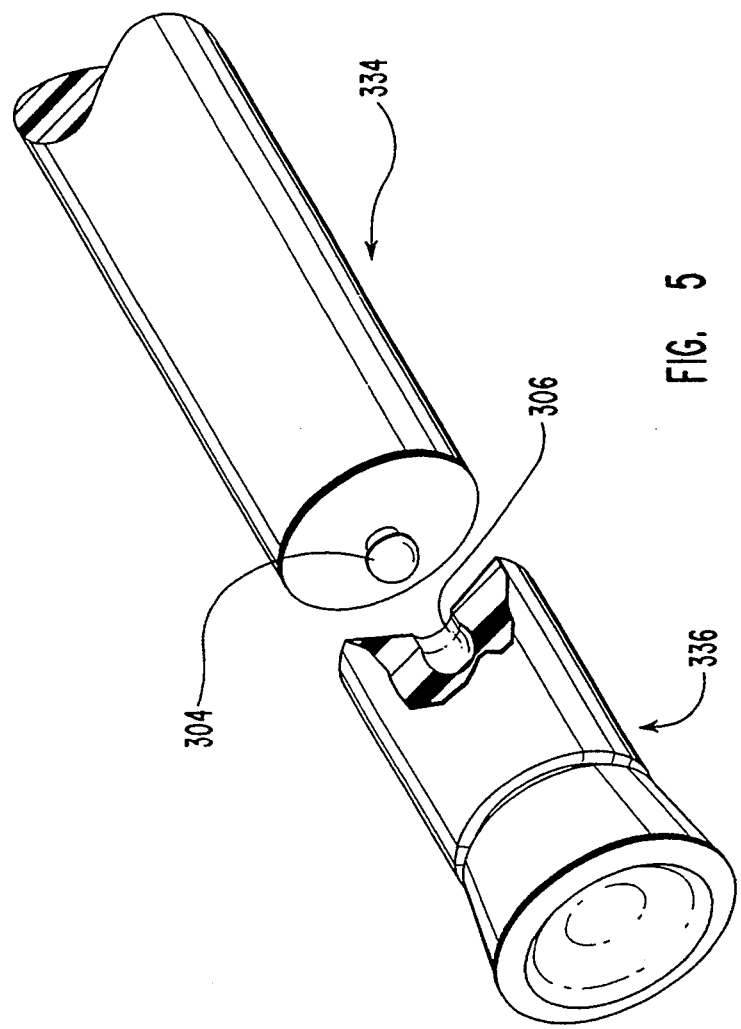

SYRINGE APPARATUS AND METHODS FOR DISPENSING VISCOUS MATERIALS

BACKGROUND OF THE INVENTION

1. Technical Field

The present invention relates to apparatus for use in dispensing viscous materials, such as dental compositions, and more specifically to syringes for dispensing viscous dental compositions in a controlled fashion.

2. Background Information

The practice of dentistry involves the use of various dental compositions which must be placed within small spaces located in cramped environments. When the composition has a low viscosity, it is a relatively simple matter to use a traditional syringe fitted with a tip having a small opening to provide precise control over the amount of composition dispensed and its placement.

Unfortunately, various dental compositions are quite viscous, and hence are difficult to force out of a conventional syringe. Others, such as resinous composite filling materials, are so highly viscous as to be virtually impossible to dispense using a conventional syringe.

In order to facilitate dispensing of viscous materials, two different tools have been developed, caulking guns and heavy-duty screw-type syringes. Both of these are capable of dispensing materials having a higher viscosity than may be dispensed from a conventional syringe.

Caulking guns and heavy-duty syringes are relatively expensive, so they are not considered disposable, although disposable tips are used to prevent the need to cleanse and sterilize tips for reuse with different patients. The remaining components of caulking guns and heavy-duty syringes must be cleansed and disinfected, however, thereby placing an unwanted burden upon the dental practitioner.

Because caulking guns utilize disposable tips, and because of the significant effort required to cleanse and disinfect them between uses, it is a standard practice to load them with enough material for use with several patients, to dispose of the tip after each patient, to affix a replacement tip, and then use the caulking gun with the next patient. Unfortunately, these devices are often splattered or otherwise contaminated during use by materials which have been in a patient's mouth. Although the splatter is rarely itself brought into contact with the mouth of a subsequent patient, and even though a dental practitioner typically uses fresh surgical gloves for each patient, it is not uncommon for the dental practitioner working on subsequent patients to touch the splatter as the caulking gun is manipulated during the course of the subsequent dental procedure, and then carry it into the patient's mouth.

Tips are not generally used with heavy duty screw-type syringes. Rather, the screw mechanism is generally used to advance material within the syringe so it can be manually removed. Not only is this subject to contamination similar in manner to the use of a caulking gun, but it is less convenient to use.

Even when using a caulking gun or heavy duty syringe, it has been found necessary to use a less viscous material than optimum in order to obtain flow. The lower viscosity formulation is thought to be weaker than a higher viscosity composite, resulting in premature failure of repairs made using a caulking gun or heavy duty syringe.

Several attempts have been made to avoid the problems of potential cross-contamination. For example, disposable syringes have been down-sized, so as to require less effort to dispense viscous materials. Many dental practitioners refuse to use these small syringes, however, because they are difficult to control when applying the strong force necessary to dispense viscous materials.

Because of the risk of infection when using caulking guns and heavy-duty syringes, and because of the difficulty of using small syringes, it is quite common for dental practitioners to forego the use of either of those devices in favor of a simple spatula or other similar tool. By way of example, this involves placement of a small quantity of composite material on a spatula and then manually packing the material into a prepared space within the patient's tooth. This is a time consuming process. In addition, small air pockets often remain within the packed material, thereby causing micro leakage to the interior of the tooth, or causing weakness in the repair. Either of these problems frequently result in premature failure of the repair. Yet, because of the problems of using other devices to dispense viscous material, many dental practitioners persist in the manual placement of viscous material using a spatula.

From the foregoing, it will be appreciated that it would be a significant advance if improved devices and associated methods for dispensing highly viscous materials could be developed for use by dental practitioners.

SUMMARY OF THE INVENTION

It is a primary object of the present invention to provide a disposable syringe and associated methods for dispensing highly viscous materials, such as resinous composite filling materials.

It is a further object to provide methods and apparatus for dispensing materials having a higher viscosity than may be dispensed using conventional caulking guns, and without air entrainment.

It is another object of the present invention to provide apparatus for dispensing highly viscous materials in a dental patient that may be more easily manipulated within the cramped environment of a patient's mouth than devices such as caulking guns.

Yet another object is to provide a syringe that is easier to manipulate and control when dispensing highly viscous materials than previous devices.

A further object of the present invention is to provide low cost apparatus for dispensing highly viscous materials so that those components that are exposed to contamination may be economically disposed of, while retaining for re-use other components which are subject to easy disinfection between uses.

Additional objects and advantages of the invention are set forth hereinbelow in the detailed description, or will be appreciated upon practice of the invention.

To achieve the foregoing objects, and in accordance with the invention as embodied and broadly described herein, the present invention provides syringe assembly apparatus and associated methods which are useful in dispensing viscous materials, such as dental compositions, in a controlled fashion.

The presently preferred embodiment of the syringe assembly of the invention includes a conventional syringe barrel having a passageway therethrough and a discharge port communicating with the passageway.

An adapter member is provided which is shaped and sized so as to nest within the syringe barrel passageway. The adapter member serves as a secondary syringe barrel. It has a bore passing through the length thereof for receiving a viscous material to be dispensed. When the adapter is nested within the passageway of the syringe body, the bore communicates with the discharge port of the syringe body. A plunger member is provided for ejecting viscous material contained within the bore through the discharge port of the syringe body.

An important feature of the invention is that the bore has a diameter substantially the same as the diameter of the discharge port at the location where the discharge port communicates with the bore. This combination results in a comfortably-sized disposable syringe assembly which is useful for dispensing highly viscous materials.

The present invention also contemplates the making and selling of adapter members for use with conventional syringes as well as part of the syringe assembly combination. Preferably, such adapter members are sized so as to be usable with conventional syringes available from various commercial sources.

The present invention also contemplates that some components may be more economically reused rather than disposed of after a single use. In particular, the invention is directed to a plunger formed of two parts, a generally reusable plunger member and a single use tip element together with means for releasable securing the two together.

BRIEF DESCRIPTION OF THE DRAWINGS

In the accompanying drawings, which represent the best mode presently contemplated for carrying out the present invention:

FIG. 1 is a cross-sectional view of a presently preferred embodiment of the apparatus of the present invention.

FIG. 2 is a cutaway cross-sectional view of another embodiment of the present invention utilizing a different type of structure and connection between the syringe barrel and the tip.

FIG. 5 is an enlarged, exploded, partially cutaway view of the end of the plunger member and replaceable tip element of FIG. 4.

DETAILED DESCRIPTION OF THE PREFERRED EMBODIMENT

Figure 3:
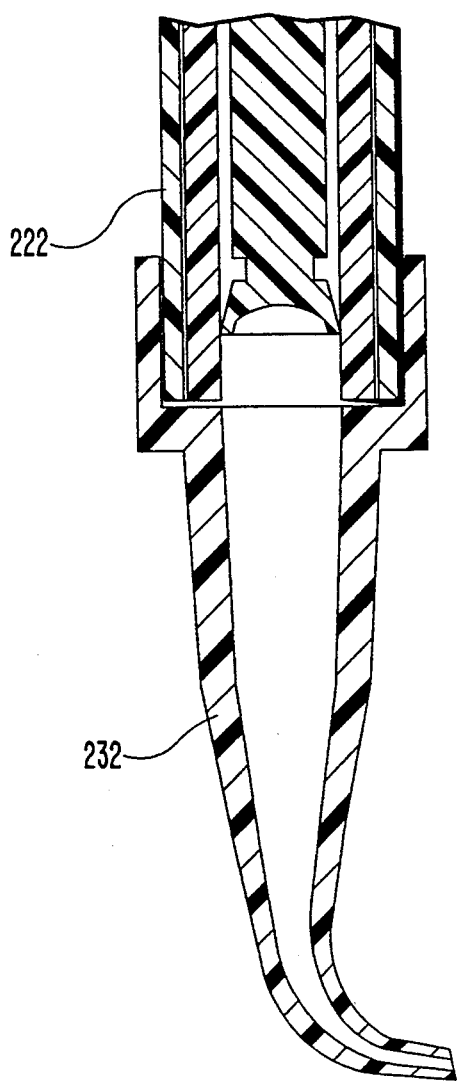
FIG. 3 is a cutaway cross-sectional view of another embodiment of the present invention utilizing yet another different type of structure and connection between the syringe barrel and the tip.

The present invention is directed to methods and apparatus for use in dispensing viscous materials, such as dental compositions, in a controlled fashion. Further, an advantage of the present invention is that it can be made and used quite inexpensively, and hence some or all of the components are readily susceptible to being disposed of after a single use. This avoids the risk of cross-contamination caused by reuse of components exposed to patient splatter, and the like, and reduces the inconvenience and cost of cleaning equipment for reuse.

FIG. 1 illustrates a presently preferred embodiment of a syringe assembly apparatus 20 in accordance with the invention. Syringe assembly 20 may be comprised of a conventional syringe barrel 22 which functions as a syringe body member. Syringe barrel 22 may be of any size, although it is contemplated that the most useful size will be in the range of about 1 to 5 cc, and most preferably in the range of about 2 to 3 cc, since a syringe barrel in that range is small enough to be easily handled and manipulated within the cramped environment of typical dental procedures, yet large enough to allow control while applying the substantial force required to dispense highly viscous materials from the syringe assembly of the invention.

A viscous material tends to retain whatever shape it has assumed. Because a viscous material resists flow into other shapes, one must apply shearing forces in order to force it to assume other shapes. This property of viscous materials makes it impractical to dispense highly viscous materials directly from the passageway 24 of syringe barrel 22 for delivery through the syringe barrel discharge port 26. Too great of a force is required to dispense highly viscous materials, such as resinous composite filling materials, through discharge port 26. A conventional syringe would either fail during the application of such force, or the dental practitioner could not be expected to apply enough force, depending upon the viscosity of the particular material to be dispensed.

It is a feature of the present invention to provide an adapter member 28 which is sized and shaped so as to fit in a nesting relationship within passageway 24 of syringe barrel 22. Preferably, the adapter member fits within passageway 24 sufficiently tightly that it will not fall out during routine use, but may be removed if such is desired.

Adapter member 28 is provided with a bore 30 therethrough which is capable of holding an amount of viscous material useful in connection with a particular purpose. It may optionally be provided with a flange 32, as illustrated. Adapter member 28 serves as a secondary syringe barrel which may be removably placed within the passageway 24 of syringe barrel 22. When adapter member 28 is inserted within passageway 24, bore 30 is aligned with discharge port 26 and communicates therewith so that viscous material ejected from bore 30 will pass into and through discharge port 26.

The use of an adapter member with its associated bore assures that the viscous material within the bore assumes a rod shape which is smaller in diameter than would be the case if it was placed directly into the passageway of the syringe barrel. This concentrates the force applied to the top of the rod of viscous material, making it easier to dispense.

More importantly, however, it has also been determined that the diameter of bore 30 should be substantially the same as the diameter of the discharge port at the location where the discharge port communicates with the bore of the adapter member. By providing a structure having relatively minor variations in the diameter along the flow path, it has been observed that the force necessary to dispense viscous material which may be contained within bore 30 from syringe assembly 20 is minimized.

It is believed that this relates to the lessening of shear forces as the "rod" of viscous material is forced through the syringe assembly. It has been determined that if the diameter of the discharge port is significantly less than that of bore 30, flow of viscous material will occur primarily from the center of the rod of material contained within the bore, with substantial resistance encountered as the flowing material is sheared from the remaining material surrounding it. The closer the diameter of the discharge port is to that of the bore, the less the shear forces.

If the diameter of the discharge port is significantly greater than that of bore 30, energy is expended in a non-useful manner as the viscous material is forced to assume a new enlarged shape, only to be subsequently forced to assume yet another shape as it is passed through tip 32, which is used for precise placement of a controlled stream of material. In addition, there is the undesirable possibility of forming lo airspaces within the viscous material.

In view of the foregoing teachings, it will be appreciated that it is better to require minimal alterations in the diameter of viscous materials prior to reaching tip 32. Nevertheless, by stating that the diameter of bore 30 should be "substantially the same" as the diameter of the discharge port at the location where the discharge port communicates with the bore of the adapter member, it should be understood that deviations can be accepted, albeit with some loss of efficiency, and one should not be able to avoid infringement of the claims of this patent by failing to strictly practice the teachings of the present invention. Indeed, as set forth below in connection with a further discussion of the preferred embodiment of FIG. 1, it may be advantageous to accept some loss in efficiency caused by variations in diameter in the flow path in order to obtain other advantages which are useful in particular situations.

Tip 32 may be of any convenient shape and size, but it is preferred that it have a bent configuration as illustrated in FIG. 1 in order to facilitate the dispensing of material into locations within the cramped environment of a patient's mouth. It is also desirable that the internal diameter of the tip be tapered toward the dispensing end so that only a small diameter stream of material is dispensed from the end of the tip. This permits greater control over placement and over the amount dispensed than would a tip having a large diameter opening at the dispensing end. Nevertheless, it should be understood that the actual size and shape of the opening of the tip at the dispensing end might be varied depending upon factors such as the viscosity of the material to be dispensed, the quantity of material to be dispensed, and the difficulty of access to the location where material is to be dispensed.

A plunger member 34 is sized and shaped so as to be useful in applying force to viscous material contained within bore 30 in a manner conventional to syringes, so that depression of the plunger member (illustrated in the fully depressed position in FIG. 1) causes material contained within bore 30 to be dispensed through discharge port 26 and out from tip 32.

In order to minimize friction between plunger member 34 and bore 30, it is preferred that most of the length of plunger member 34 have a diameter less than that of the bore, taking care to avoid making the diameter so small as to lose the strength required to serve its function. A plunger tip 36 is advantageously formed at the end of the plunger member in order to scrape the sides of the bore and serve as a ram to effect the actual dispensing force upon material contained within bore 30. Although plunger tip 36 may take many forms, it is presently preferred that it have a generally convex surface 36a for contact with the material to be dispensed, and a small circumferential trough 36b rearwardly of the convex surface. Advantageously, plunger tip 36 tapers from the lesser diameter of the main portion of plunger member 34 to the larger diameter at the very end thereof, such taper being indicated in FIG. 1 by use of reference numeral 36c.

It may be desirable to prepackage suitable viscous materials within the adapter member of the present invention. Placement of the plunger member 34 will seal one end of bore 30, or some other type of cap or seal could be provided. It is useful to provide a neck 38 at the other end of the adapter member in order to center bore 30 within discharge port 26 during use, but such a neck may also provide a surface which can accommodate a cap (not shown) or other means for sealing the end of the adapter member 28. In the embodiment of FIG. 1, it should be observed that neck 38 may have a diameter slightly smaller than bore 30, but by virtue of the fact that the neck will nest against the discharge port 26, the diameter of the neck is very close to that of the discharge port. This illustrates that slight variations in the diameters of the various components come within the scope of the present invention.

It should be understood that although it is presently contemplated that both ends of a preloaded adapter member will be capped, another alternative would be to leave either or both ends exposed and to place the adapter member within a sealed package in order to prevent contamination or curing or spoiling of material contained within bore 30.

The syringe assembly 20 is used by depressing the plunger member 34 in conventional fashion. A flange 40, or other well known equivalent such as finger rings, should be provided at the end of the syringe barrel 22 in order to provide a surface to use in opposition to the force placed on the end of plunger member 34.

The preferred embodiment of FIG. 1 illustrates the use of a conventional luer-type fitting for securing tip 32 to syringe barrel 22. Finger tabs 42 can be provided to assist in making a tight connection. Alternatively, as seen in FIGS. 2 and 3, other means for attaching the tip to the syringe barrel may be employed. In FIG. 2, tip 132 may be attached to syringe barrel 122 by means of adhesive or welding, or the like. In the embodiment of FIG. 2, it is useful to provide a step 102 at the end of the passageway of syringe barrel 122 in order to provide a stop against which the end of adapter member 128 may rest. FIG. 3 illustrates another alternative configuration, wherein the tip 232 is again secured to syringe barrel 222 by adhesive or other well-known means. In both FIGS. 2 and 3, the bore of the adapter member has substantially the same diameter as the discharge port of the syringe barrel at the location where they intercommunicate.

The special geometry and relationship of the various elements as described above work together to permit a comfortably-sized syringe assembly to be used to dispense highly viscous materials with greater control than heretofore possible. By manufacturing the components out of suitable low-cost medical grade materials, such as polypropylene, it is economical to use them once and then dispose of them.

It may be desirable, however, to construct some components, particularly the plunger member, out of stronger materials, such as metal alloys or Delrin. This may increase the cost to the point where it becomes desirable to reuse the plunger member rather than to dispose of it after a single use. Yet, the tip of the plunger member is subject to wear or may be difficult to economically clean, so as to require replacement even though the remainder of the plunger element is still usable.

Figure 4:
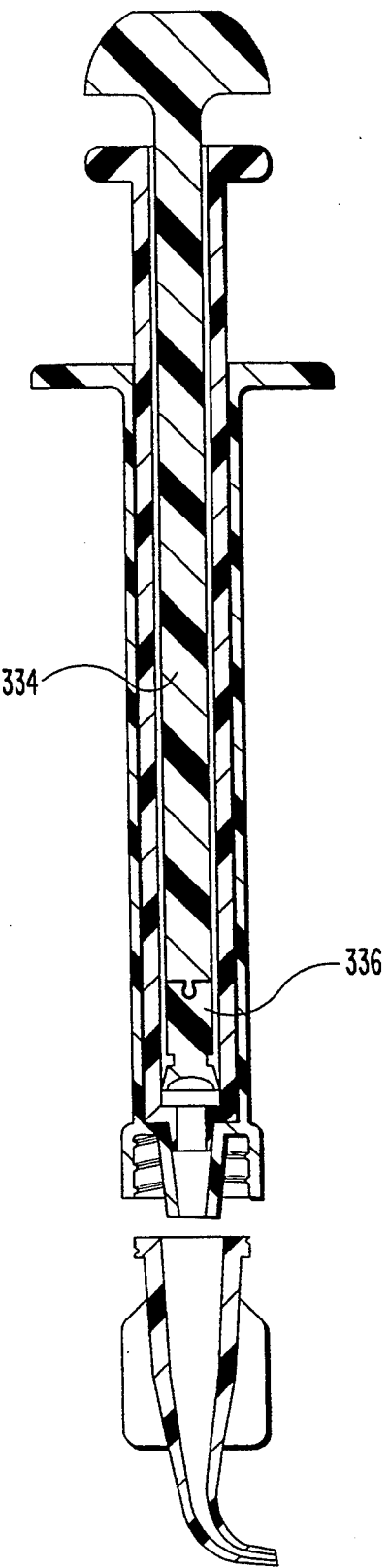
FIG. 4 is a cross-sectional view of another preferred embodiment of the present invention like that of FIG. 1, but wherein the plunger member is provided with a replaceable tip element.

FIG. 4 illustrates a syringe assembly like that of FIG. 1, except that plunger member 334 is provided with a removable plunger tip element 336. FIG. 5 illustrates the end of plunger member 334 and plunger tip element 336 in greater detail. Plunger member 334 may be made of any convenient material, including relatively expensive materials such as Delrin or metal alloys, it being anticipated that the plunger member can be used again and again. The plunger tip element in FIGS. 4 and 5 is removably attached to the end of the plunger member. As best seen in FIG. 5, the presently preferred means for attaching the plunger tip element to the plunger member involves the use of a ball element 304 on the end of plunger member 334, and a corresponding socket 306 on the end of plunger tip element 336. By making the plunger tip element out of a resilient material, it is possible to securely affix the plunger tip element to the plunger member, while providing for easy removal and replacement of a new plunger tip element after each use. Of course, it will be appreciated that many other specific means could be used to removably attach a plunger tip element to the plunger member.

From the foregoing, it will be appreciated that the present invention provides a syringe assembly and associated components and methods which are susceptible to being made so inexpensively as to be disposable, thereby avoiding the risk of cross-contamination caused by reuse of exposed components, and also avoiding the need for cleansing and disinfecting of equipment between uses. Yet, the apparatus and methods of the present invention are suitable for dispensing highly viscous materials, such as resinous composite filling materials. Use of a conventional syringe barrel with an adapter in accordance with the teachings set forth herein provide a syringe assembly that is easy to manipulate and control while maintaining the other advantages of disposable equipment. The present invention solves the problems which have caused many dental practitioners to resort to use of a spatula to place viscous materials rather than use tools such as caulking guns, heavy-duty syringes, or small syringes to dispense such viscous materials.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. A syringe assembly for use in dispensing viscous materials, said syringe assembly comprising:
    a syringe body member forming a first syringe barrel,
        said syringe body member having a passageway passing through the length thereof, and
        said syringe body member having a discharge port smaller in diameter than said passageway and communicating with the passageway at a distal end;
    an adapter member forming a secondary syringe barrel that is nested essentially completely within said first syringe barrel so as to extend within the first syringe barrel substantially through the entire length of the first syringe barrel to said distal end,
        said adapter member having a bore passing through the length thereof for receiving a viscous material to be dispensed,
        said bore communicating with the discharge portion of the syringe body member of the first syringe barrel,
        said bore of the adapter member having a diameter substantially the same as the diameter of said discharge port of the first syringe barrel and said adapter member extending to and contacting without obstruction the first syringe barrel at the location where the discharge port of the first syringe barrel communicates with the bore of the adapter member; and
    a plunger member situated within the bore of the adapter member for ejecting viscous material contained within said bore through the discharge port of the syringe body member.

2. A syringe assembly as defined in claim 1, wherein the adapter member is preloaded with a viscous material.

3. A syringe assembly as defined in claim 1, wherein the adapter member is provided with a neck member which extends at least partially into the discharge port.

4. A syringe assembly as defined in claim 1, wherein the end of the adapter member is stepped and the syringe body member passageway has a corresponding step in order to align the adapter member within the passageway.

5. A syringe assembly as defined in claim 1, wherein the plunger member further comprises a removable plunger tip element.

6. A syringe assembly as defined in claim 5, wherein the plunger tip element is secured to the plunger member by means for attaching the tip element to the plunger member.

7. A syringe assembly as defined in claim 6, wherein the means for attaching the tip element to the plunger member comprises a ball and a socket.

8. A syringe assembly as defined in claim 7, wherein the end of the plunger element is provided with a ball, and the end of the plunger tip element is provided with a socket which will mate with such ball, and wherein the socket of the plunger tip element is formed from a resilient material so that it may be attached or detached from the ball of the plunger member.

9. In a syringe apparatus having a syringe barrel having a passageway therethrough and a discharge port smaller in diameter than said passageway, said discharge port located at a distal end of the passageway for dispensing viscous materials, the improvement comprising:
    an adapter member comprising means for forming a secondary syringe barrel of reduced diameter relative to said passageway and that is essentially completely nested within the passageway of the syringe barrel such that the secondary syringe barrel extends into the conventional syringe barrel up to said distal end thereof,
    said adapter member having a bore passing through the length thereof for receiving a viscous material to be dispensed,
        said bore communicating with the discharge portion of the syringe barrel when the adapter member is inserted in the passageway of said syringe barrel;

said bore of the adapter member having a diameter substantially the same as the diameter of said discharge port and said adapter member extending to and contacting without obstruction the syringe barrel at the location where the discharge port of the syringe barrel communicates with the bore of the adapter member; and a plunger member situated within the bore of the adapter member for ejecting viscous material contained within said bore through the discharge port of the syringe barrel.

10. An apparatus as defined in claim 9, wherein the adapter member is preloaded with a viscous material.

11. An apparatus as defined in claim 9, wherein the adapter member is further provided with a neck member which extends at least partially into the discharge port of the syringe barrel with which it is to be used.

12. An apparatus as defined in claim 9, wherein the end of the adapter member is stepped and the syringe barrel passageway is correspondingly stepped in order to align the adapter member within the passageway.

13. An apparatus as defined in claim 9, wherein the plunger member further comprises a removable plunger tip element.

14. An apparatus as defined in claim 13, wherein the plunger tip element is secured to the plunger member by means for attaching the tip element to the plunger member.

15. An apparatus as defined in claim 14, wherein the means for attaching the tip element to the plunger member comprises a ball and a socket configuration.

16. An apparatus as defined in claim 15, wherein the end of the plunger element is provided with a ball projecting therefrom, and the end of the plunger tip element is provided with a socket thereinto which will mate with said ball, and wherein the socket of the plunger tip element is formed from a resilient material so that it may be attached or detached from the ball of the plunger member.

* * * * *

UNITED STATES PATENT AND TRADEMARK OFFICE
CERTIFICATE OF CORRECTION

PATENT NO. : 5,445,523
DATED : August 29, 1995
INVENTOR(S) : DAN E. FISCHER et al.

It is certified that error appears in the above-indentified patent and that said Letters Patent is hereby corrected as shown below:

Column 2, line 19, "result" should be --results--
Column 3, line 26, "releasable" should be --releasably--
Column 5, line 10, delete "lo"
Column 5, line 59, "sides-" should be --sides--

Signed and Sealed this

Fourteenth Day of May, 1996

Attest:

BRUCE LEHMAN

*Attesting Officer*          *Commissioner of Patents and Trademarks*